United States Patent [19]

Patel

[11] Patent Number: 5,252,262
[45] Date of Patent: Oct. 12, 1993

[54] METHOD OF ATTACHING A HAPTIC TO AN OPTIC OF AN INTRAOCULAR LENS

[75] Inventor: Anilbhai S. Patel, Arlington, Tex.

[73] Assignee: Nestle S.A., Vevey, Switzerland

[21] Appl. No.: 833,872

[22] Filed: Feb. 11, 1992

[51] Int. Cl.⁵ .............................................. B29D 11/00
[52] U.S. Cl. .................................. 264/1.4; 156/272.8; 219/121.66; 264/1.7; 264/22; 264/155; 623/6
[58] Field of Search ................... 264/1.4, 1.7, 22, 155; 623/6; 156/272.8, 304.2; 219/121.61, 121.8, 121.67, 121.66

[56] References Cited

U.S. PATENT DOCUMENTS

| | | |
|---|---|---|
| 4,786,445 | 11/1988 | Portnoy et al. . |
| 4,834,749 | 5/1989 | Orlosky ................................. 264/1.4 |
| 4,834,751 | 5/1989 | Knight et al. . |
| 4,843,209 | 6/1989 | Milligan . |
| 4,863,539 | 9/1989 | Lee et al. . |
| 4,894,062 | 1/1990 | Knight et al. . |
| 5,074,942 | 12/1991 | Kearns et al. ......................... 156/305 |
| 5,118,452 | 6/1992 | Lindsey et al. ................... 156/272.8 |

FOREIGN PATENT DOCUMENTS 63-206240 8/1988 Japan .

Primary Examiner—Jeffrey Thurlow
Assistant Examiner—Mathieu Vargot
Attorney, Agent, or Firm—Jeffrey S. Schira

[57] ABSTRACT

A method for attaching a pair of colored haptics (20) to an optic (10) of an intraocular lens (1), containing the steps of providing the peripheral edge (17) of the optic (10) with a pair of holes (12), inserting the end portions (21) of the haptics (20) into the holes (12), aiming a laser emitting radiation within the visible spectrum at the end portion (21) of the haptic within the hole (12) in the optic (10) and firing the laser so that the radiation passes through the optic (10) essentially without absorption and is absorbed by the haptic (20), thereby causing the haptic (20) to fuse with the optic (10).

55 Claims, 5 Drawing Sheets

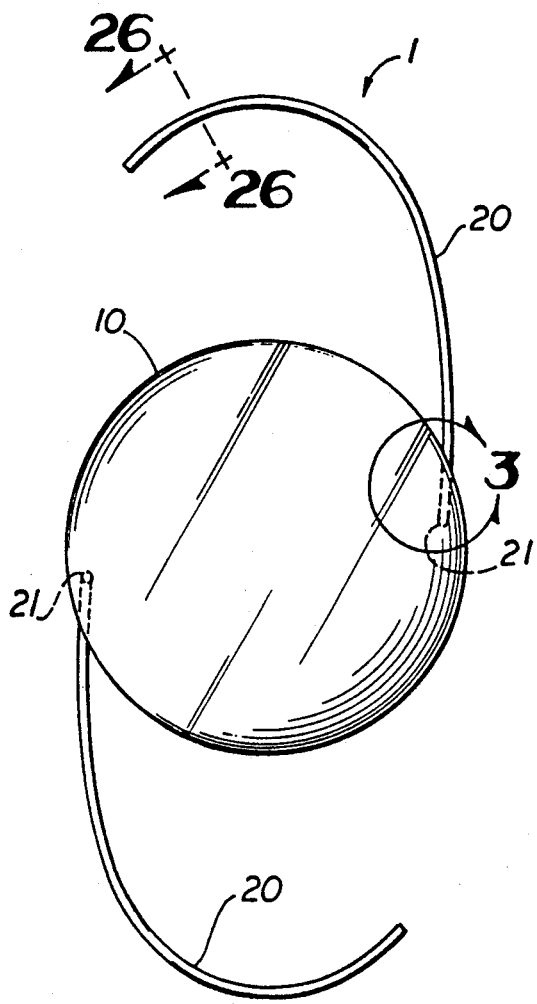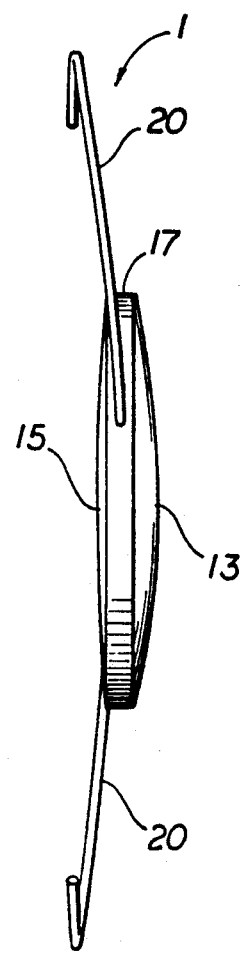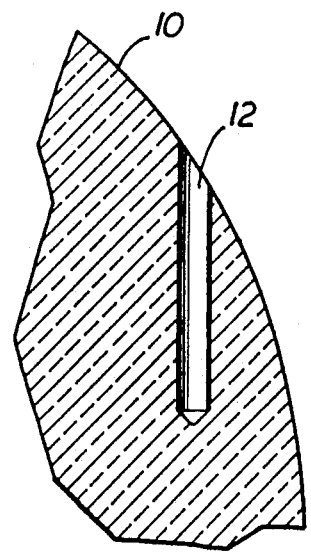
FIG 1  FIG 2
FIG 3

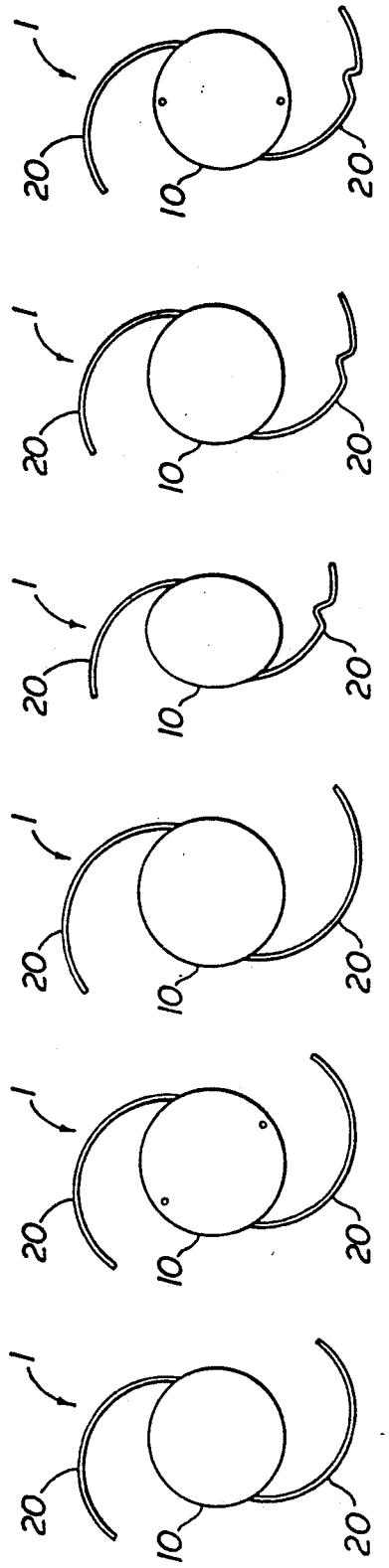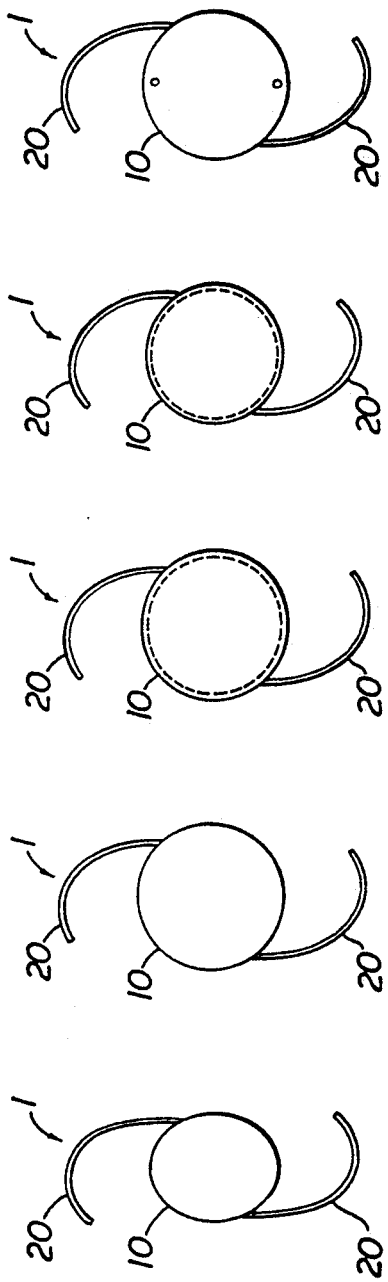

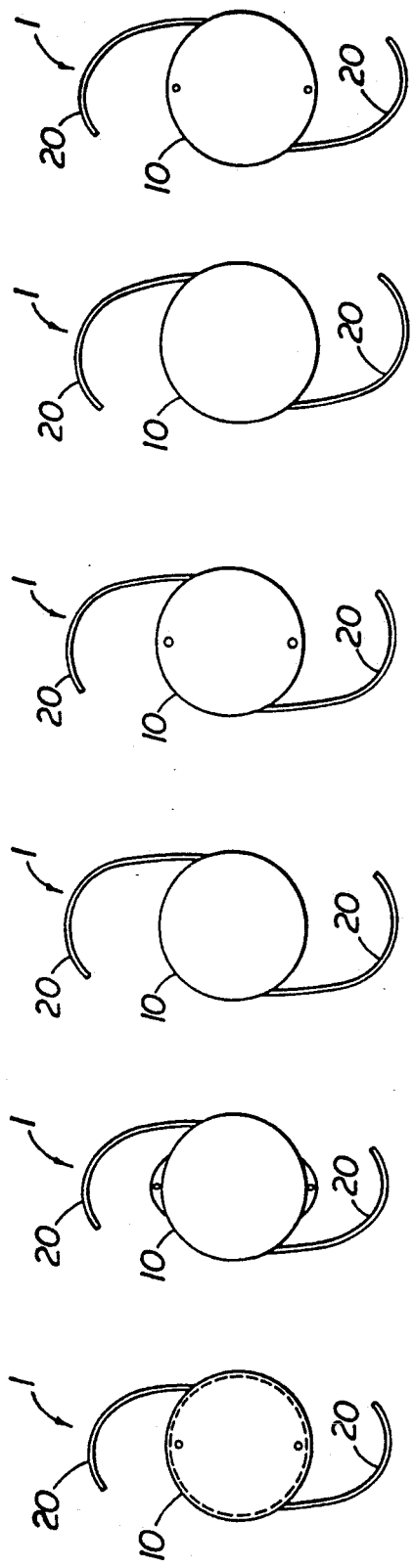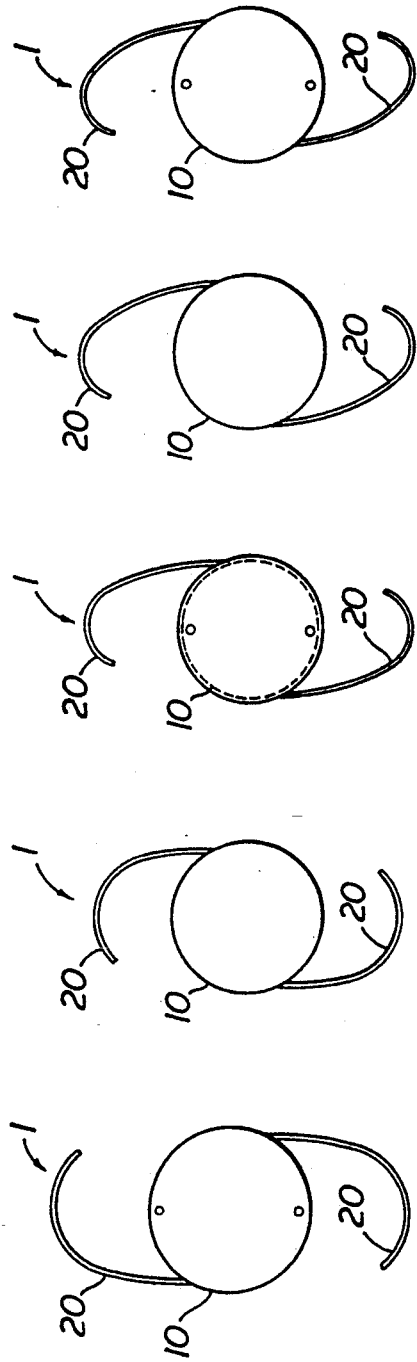

METHOD OF ATTACHING A HAPTIC TO AN OPTIC OF AN INTRAOCULAR LENS

BACKGROUND OF THE INVENTION

The present invention relates to intraocular lenses, particularly to methods for attaching a haptic to an optic using laser welding.

Intraocular lenses have been known since about 1950. They are used to replace the natural lenses of eyes that have been damaged by trauma or disease, such as cataracts. A typical intraocular lens ("IOL") comprises an artificial lens ("optic") and at least one support member ("haptic") for positioning the IOL within the capsular bag of the eye. The optic may be formed from any of a number of different materials, including polymethylmethacrylate (PMMA) and acrylics, and it may be hard, relatively flexible or even fully deformable so that the IOL can be rolled or folded and inserted through a relatively small incision in the eye. The haptic generally is made of some resilient material, such as polypropylene or flexible copolymers of PMMA. IOL's may be characterized as either "one-piece" or "multi-piece." With one-piece IOL's, the haptic and the optic are formed integrally as a blank and the IOL is then milled or lathed to the desired shape and configuration. The multi-piece IOL's are formed either by attaching the haptic to a pre-formed optic or by molding the optic around an end of the haptic.

U.S. Pat. Nos. 4,834,751 and 4,894,062 (both to Knight, et al.) describe haptic attachment methods whereby the haptic and an anchoring member are joined and the optic is molded around the end of the haptic having the anchoring member. While these methods provide strong haptic-optic interlock, the procedure for molding an optic around the previously joined haptic and anchor member is complex and requires special care to maintain the haptic in place while the optic material is cured, and to remove the cured IOL from the mold without damaging the haptic.

Many methods for attaching a haptic to a pre-formed optic are known, including those involving the use of adhesives. If an adhesive is used to attach a haptic to an optic, the adhesive must be strong, biologically inert and resistant to degradation by bodily fluids. At present, there are few materials that satisfy all these requirements. In addition, there will always be a concern that the adhesive will deteriorate over time, resulting in loose or detached haptics within the eye.

Other more common methods for attaching a haptic to a pre-formed optic involve the use of heat. One such haptic attachment method involves drilling intersecting holes into the periphery of an optic and inserting one end of the haptic into one of the holes. A heated probe is inserted through the other hole, contacting the embedded end of the haptic and causing a portion of it to melt and flow laterally into the second hole. When the embedded haptic end cools and hardens, a mechanical interlock with the optic is formed. A similar method is disclosed in U.S. Pat. No. 4,104,339 (Fetz, et al.), where a haptic hole is made in the peripheral edge of an optic, the haptic end is inserted into the hole and then an inductively heated thin probe is pushed through the posterior face of the optic into contact with the haptic end to form a crimped connection between the haptic and the optic. This is currently the most common method used for attaching haptics to optics. However, this method damages the optic surface where the heated probe is pushed through to the haptic end and thus, compromises optical performance.

Another similar method is disclosed in U.S. Pat. No. 4,307,043 (Chase, et al.), where a hole having threaded recesses is made through a portion of the optic (the hole being essentially parallel to the plane of the optic) and one end of a haptic is inserted through the hole so that it projects beyond the optic. Heat is then applied to the haptic end projecting beyond the optic to melt a portion of it, which fills the threaded portions of the hole. When the haptic material hardens, a mechanical interlock with the optic is formed. This heat attachment technique is disadvantageous because skilled technicians and precise equipment alignment are required.

U.S. Pat. No. 4,786,445 (Portnoy, et al.) discloses another haptic attachment method which involves making a cavity having a shoulder in the periphery of an optic. The haptic end is inserted into the cavity and laser energy of a near infrared wavelength is transmitted through the optic to the haptic, causing the haptic end to melt and flow into the shoulder of the cavity. When the end hardens, a mechanical interlock between the haptic and the optic is formed. Although this method avoids some of the problems of the prior-mentioned methods, there are other disadvantages. Because the haptic end is melted to form a shoulder within the cavity of the optic, there is a likelihood of variation in haptic length, both between individual IOL's and between individual haptics attached to the same IOL.

U.S. Pat. No. 4,843,209 (Milligan) discloses a method of attaching a haptic to an optic using laser energy. However, the method disclosed uses a high-powered neodymium:yttrium-aluminum-garnet (Nd:YAG) laser that emits radiation in the non-visible spectrum, necessitating the use of a Helium-Neon (HeNe) aiming laser, and resulting in exacting Nd:YAG/HeNe laser alignment requirements. Furthermore, the method disclosed in this patent does not rely on a differential in laser energy absorption between the haptic and the optic to prevent optic damage (both the optic and the haptic being disclosed as comprising PMMA) and, instead, the disclosed method must carefully balance the amount of laser energy used with the time of exposure to insure that the optic is not damaged. The haptic absorbs the laser energy more readily than the optic because the optic has a smooth, flat surface while both the haptic and the hole in the optic contain a series of interlocking ridges that diffusion and deflect the radiation within the haptic This absorption method is inefficient, requiring the use of a relatively high laser power level (on the order of 50 watts) and is unnecessarily complex and expensive because of the difficulty in forming the ridges in the hole and on the haptic.

Accordingly, a need has continued to exist for a simple, reliable method of attaching a haptic to an optic of an intraocular lens without damaging the optic or otherwise distorting the optical properties of the optic.

BRIEF SUMMARY OF THE INVENTION

The present invention improves upon prior art methods of attaching a haptic to an optic by providing a method for using laser energy to attach a haptic to an optic without damaging the optic while producing a strong mechanical interlock between the haptic and the optic. This is accomplished by forming a single, smooth mounting hole in the peripheral edge of an optic in the plane normal to the optical axis of the optic, inserting the smooth end of a colored haptic into the hole and transmitting laser energy within the visible spectrum through the optic to the portion of the haptic within the optic, whereby the haptic is heated to the melting temperature of the haptic material and this heat fuses the haptic and the optic, forming a solid fusion and integrally welding the haptic within the optic. The use of a colored haptic and a laser transmitting energy in the visible spectrum allows the laser energy to be transmitted through the optic without damaging the optic, while at the same time, increasing the absorption of the laser energy by the haptic. Therefore, equipment alignment tolerances are more generous. The use of a visible laser energy source also is less hazardous than other invisible forms of laser energy because the laser beam is easily seen and thus more readily avoided.

Accordingly, one objective of the present invention is to provide a method of attaching an intraocular lens haptic to an optic that does not require mechanical deformation of the optic.

Another objective of the present invention is to provide a method of attaching an intraocular lens haptic to an optic that does not damage the optic.

Another objective of the present invention is to provide a method of laser welding an intraocular lens haptic to an optic that does not require precise alignment of the welding laser.

Another objective of the present invention is to provide a method of attaching an intraocular lens haptic to an optic that is simple and inexpensive.

Still another objective of the present invention is to provide a method of attaching an intraocular lens haptic to an optic using a visible laser.

A further objective of the present invention is to provide a method of attaching an intraocular lens haptic to an optic that requires only a single haptic mounting hole in the optic.

Another objective of the present invention is to provide a method of attaching an intraocular lens haptic having a colored core to an optic.

These and other objectives and advantages of the present invention will become apparent from the detailed description, drawings and claims that follow.

BRIEF DESCRIPTION OF THE DRAWING

FIG. 1 is a posterior plan view of a typical IOL made in accordance with the methods of the present invention.

FIG. 2 is an elevation view of the IOL illustrated in FIG. 1.

FIG. 3 is a fragmentary cross-section of the IOL illustrated in FIG. 1 with the haptic removed and taken at insert circle 3.

FIGS. 4-25 are anterior plan view of alternative embodiments of IOL's made in accordance with the methods of the present invention.

DETAILED DESCRIPTION OF THE INVENTION

Figure 26:
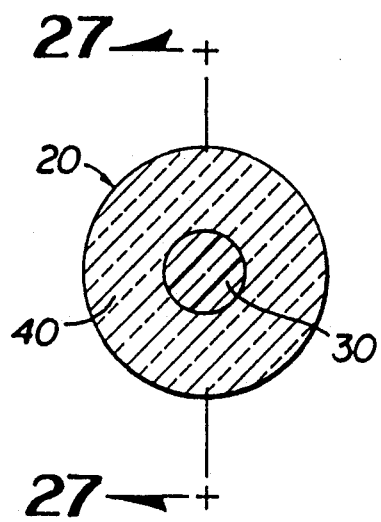
FIG. 26 is a cross-section of a first embodiment of the haptic made in accordance with the methods of the present invention taken at line 26—26 in FIG. 1.

As can be seen in FIG. 1 and 2, IOL 1 includes an optic 10 and at least one haptic 20. As illustrated in FIGS. 4-25, haptics 20 may be configured in any of a number of ways and the optic 10 may have any of a number of closed-curve shapes, such as a circle, an oval or an ellipse. Although several suitable optics 10 and haptics 20 configurations are illustrated in FIGS. 1, 2 and 4-25, other suitable shapes, sizes and configurations may also be used.

Optic 10 has anterior face 13, posterior face 15 and peripheral edge 17. Optic 10 may be made of any suitable, biocompatible transparent plastic, such as PMMA, polycarbonate and copolymers of esters of acrylic acid and methacrylic acid. Optic 10 is preferably between 4.50 millimeters (mm) and 7.00 mm across.

Figure 27:
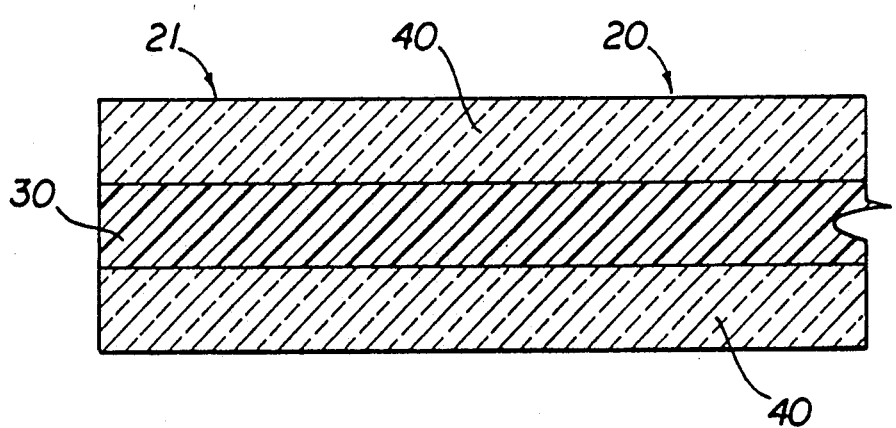
FIG. 27 is a longitudinal cross-section of an end portion of the first embodiment of the haptic of the present invention taken perpendicularly to the cross-section illustrated in FIG. 26 at line 27—27.
Figure 28:
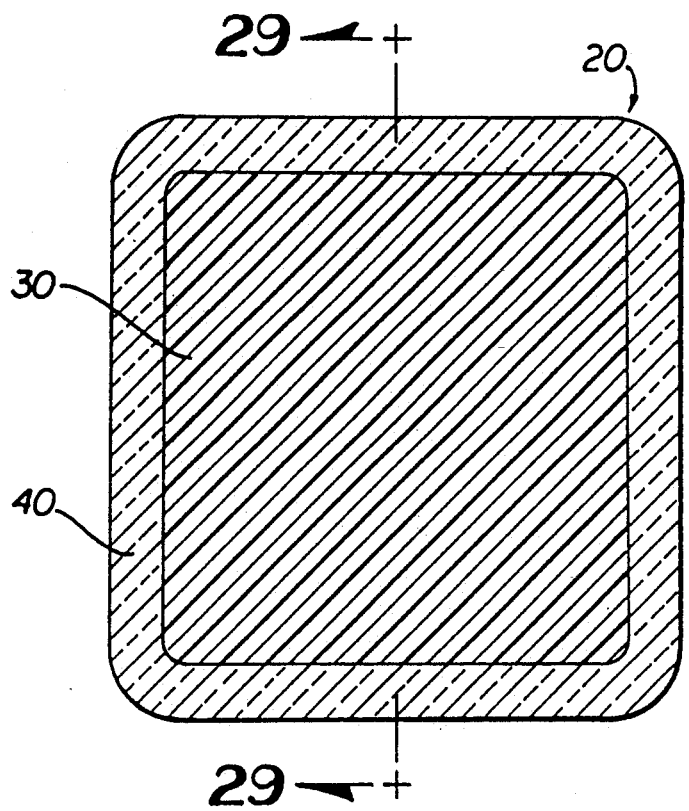
FIG. 28 is a cross-section of a second embodiment of the haptic made in accordance with the methods of the present invention similar to FIG. 26.
Figure 29:
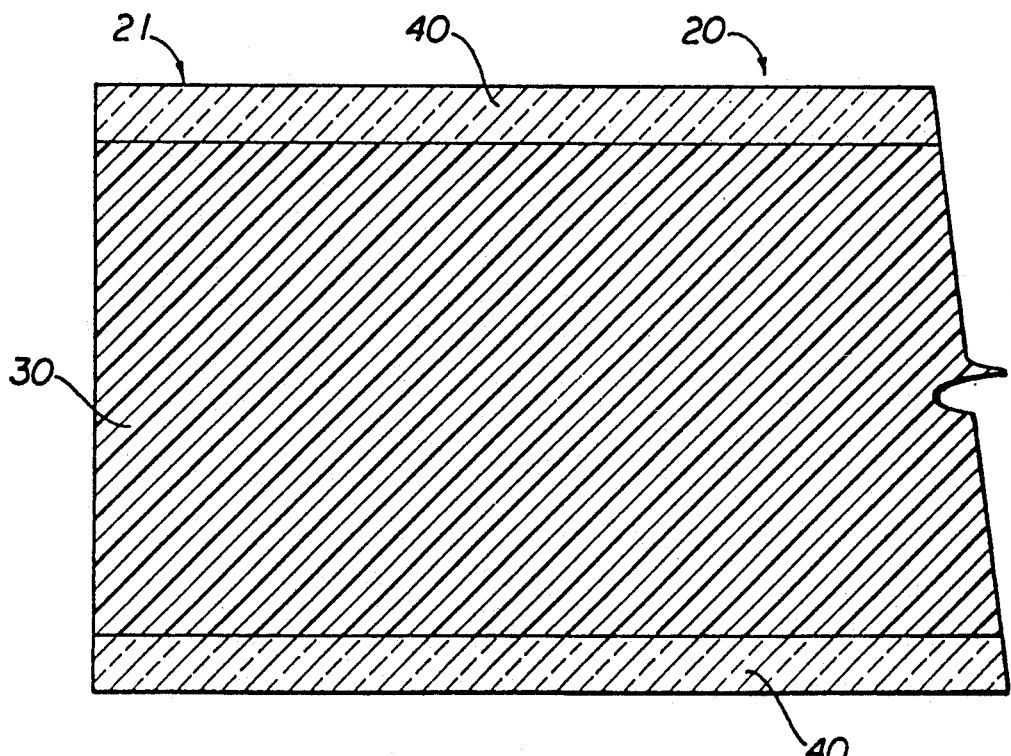
FIG. 29 is a longitudinal cross-section of an end portion of the second embodiment of the haptic of the present invention taken perpendicularly to the cross-section illustrated in FIG. 28 at line 29—29.

Haptics 20 are formed separately from optic 10 by injection molding, extrusion, thermal-drawing or any other suitable method. Haptic 20 may be of any suitable cross-sectional shape, such as round, as illustrated in FIGS. 26 and 27, rectangular with rounded corners, as illustrated in FIGS. 28 and 29, oval, elliptical, hexagonal or other geometric shape and is preferably smooth and at least end portion 21 of haptic 20 to be attached to optic 10 must be a colored material. Alternatively, as can be seen in FIGS. 26-29, haptic 20 may have a colored core 30 surrounded by a clear sheath 40. The use of core 30 surrounded by sheath 40 helps to minimize any possible leaching of the pigment used to color core 30 from haptic 20. Round haptic 20 (illustrated in FIGS. 26 and 27) generally has a diameter of approximately between 0.105 and 0.175 mm, with between approximately 0.127 and 0.152 mm being preferred, and the diameter of core 30 may be anywhere within the same range as the diameter of haptic 20. Rectangular haptic 20 (illustrated in FIGS. 28 and 29) preferably has a width of between approximately 0.11 and 0.14 mm and a height of approximately between 0.14 and 0.16 mm, for example, 0.127 mm wide by 0.152 mm high with the dimensions of core 30 approximating the overall dimensions of haptic 20. Haptic 20 may be made of any of a number of thermoplastics such as PMMA, polypropylene, polyimides and polyvinylidene difluoride and may be either different from or the same material as used in optic 10. If the material used to form haptic 20 is naturally non-colored, the material must either include a pigment, a dye or be combined with a colored material. One suitable haptic material is available from Rohm and Haas under the tradename VS100 which, upon adding copper phthalocyanine, gives the raw material necessary for forming colored haptics 20. Other preferred haptic materials include PMMA with a copper phthalocyanine-doped core 30 and blue polypropylene.

The laser (not shown) used to weld haptic 20 to optic 10 must emit radiation in the visible spectrum, approximately between 400 and 700 nanometers (nm) and is preferably a continuous wave (CW) laser. Visible wavelength laser energy will be at least partially absorbed by the colored haptic material, regardless of the specific wavelength of energy used or the color of haptic 20; however, it is preferable that the laser energy spectrum used be matched with the absorption spectrum of the material used to form haptic 20 or core 30. For example, if haptic 20 or core 30 is blue, it is generally preferred that the visible laser energy spectrum have some wavelengths in the deep blue, green or red portions of the visible spectrum absorbed by haptic 20 or core 30. Such a spectrum is emitted from Krypton, Argon or tunable dye lasers for a copper phthalocyanine-doped PMMA haptic 20.

As best seen in FIG. 3, hole 12 in optic 10 may be made in any suitable manner and be formed either after optic 10 has been formed, such as by drilling, or optic 10 may be formed with hole 12 pre-formed. Hole 12 is preferably smooth and less than 1 mm deep and should be only slightly larger in diameter than the maximum cross-sectional dimension of haptic 20 so that haptic 20 fits snugly within hole 12.

To attach haptic 20 to optic 10, end portion 21 of haptic 20 is inserted fully into hole 12. The laser (not shown) is aimed at end portion 21 of haptic 20 within hole 12 in optic 10 and fired. The laser energy is fully transmitted through transparent optic 10 without damaging optic 10 while the pigment or dye in haptic 20 or in core 30 absorbs the laser energy and heats to a temperature sufficient to melt end portion 21 and fuse end portion 21 to optic 10 within hole 12. The laser energy level needed to fuse haptic 20 and optic 10 will vary with the materials used for optic 10, haptic 20 and core 30, but generally will be less than 5 watts. By way of example, when an Argon (CW) or Krypton (CW) laser is used, haptic 20 is made from the colored VS100 material (PMMA with a copper phthalocyanine-doped core) and optic 10 is made from PMMA, the laser output required to fuse haptic 20 and optic 10 is approximately between ¼ and 2 watts with a laser exposure time of approximately between 1 and 3 seconds when a laser spot size of approximately 100 microns is used.

This description is given for purposes of illustration and explanation. It will be obvious to those skilled in the relevant art that modifications may be made to the invention as described herein without departing from its scope or spirit.

I claim:

1. A method for attaching at least one colored haptic to an optic of an intraocular lens, comprising the steps of:
    a. providing a peripheral edge of the optic with at least one hole;
    b. inserting an end of the haptic into the hole;
    c. aiming at a portion of the haptic within the hole a laser having a power level of less than 5 watts and emitting radiation within a visible spectrum that is matched to the radiation absorption spectrum of the colored haptic; and
    d. firing the laser so that the radiation passes through the optic essentially without absorption and is absorbed by the haptic, thereby causing the haptic to fuse with the optic.

2. The method of claim 1 wherein the haptic comprises a violet-colored material.

3. The method of claim 1 wherein the haptic comprises a green-colored material.

4. The method of claim 1 wherein the haptic comprises a blue-colored material.

5. The method of claim 4 wherein the blue-colored material comprises polymethylmethacrylate with a copper phthalocyanine-doped core.

6. The method of claim 1 wherein the optic comprises transparent plastic.

7. The method of claim 6 wherein the plastic comprises polymethylmethacrylate.

8. The method of claim 6 wherein the plastic comprises polycarbonate.

9. The method of claim 6 wherein the plastic comprises copolymers of esters of acrylic acid and methacrylic acid.

10. The method of claim 1 wherein the haptic comprises thermoplastic.

11. The method of claim 10 wherein the thermoplastic comprises copolymers of esters of acrylic acid and methacrylic acid.

12. The method of claim 10 wherein the thermoplastic comprises polymethylmethacrylate.

13. The method of claim 10 wherein the thermoplastic comprises a polyimide.

14. The method of claim 10 wherein the thermoplastic comprises polyvinylidene difluoride.

15. The method of claim 10 wherein the thermoplastic comprises polypropylene.

16. The method of claim 1 wherein the visible spectrum comprises radiation of wavelength from about 400 nanometers to about 700 nanometers.

17. The method of claim 1 wherein the laser comprises an Argon laser.

18. The method of claim 1 wherein the laser comprises a tunable dye laser.

19. The method of claim 1 wherein the laser comprises a Krypton laser.

20. The method of claim 1 wherein the hole is drilled in the peripheral edge of the optic.

21. The method of claim 1 wherein a shape of the optic is a closed curve.

22. A method for attaching at least one colored haptic to an optic of an intraocular lens, comprising the steps of:
    a. drilling at least one hole in a peripheral edge of the optic;
    b. inserting an end of the haptic into the hole;
    c. aiming at a portion of the haptic within the hole a laser having a power level of less than 5 watts and emitting radiation within a wavelength range of approximately between 400 nanometers and 700 nanometers that is matched to the radiation absorption spectrum of the colored haptic; and
    d. firing the laser so that the radiation passes through the optic essentially without absorption and is absorbed by the haptic, thereby causing the haptic to use with the optic.

23. The method of claim 22 wherein the haptic comprises thermoplastic.

24. The method of claim 23 wherein the thermoplastic comprises copolymers of esters of acrylic acid and methacrylic acid.

25. The method of claim 23 wherein the thermoplastic comprises polymethylmethacrylate.

26. The method of claim 25 wherein the haptic further comprises a copper phthalocyanine-doped core.

27. The method of claim 23 wherein the thermoplastic comprises a polyimide.

28. The method of claim 23 wherein the thermoplastic comprises polyvinylidene difluoride.

29. The method of claim 23 wherein the thermoplastic comprises polypropylene.

30. The method of claim 22 wherein the optic comprises transparent plastic.

31. The method of claim 30 wherein the plastic comprises polymethylmethacrylate.

32. The method of claim 30 wherein the plastic comprises polycarbonate.

33. The method of claim 30 wherein the plastic comprises copolymers of esters of acrylic acid and methacrylic acid.

34. The method of claim 22 wherein the laser comprises an Argon laser.

35. The method of claim 22 wherein the laser comprises a tunable dye laser.

36. The method of claim 22 wherein the laser comprises a Krypton laser.

37. The method of claim 22 wherein a shape of the optic is a closed curve.

38. A method for attaching at least one colored haptic to an optic of an intraocular lens, comprising the steps of:
   a. forming the haptic from polymethylmethacrylate with a copper phthalocyanine-doped core;
   b. drilling a peripheral edge of the optic with at least one hole;
   c. inserting an end of the haptic into the hole;
   d. aiming at a portion of the haptic within the hole an Argon laser having a power level of less than 5 watts and emitting radiation within the visible spectrum that is matched to the radiation absorption spectrum of the colored haptic; and
   e. firing the laser so that the radiation passes through the optic essentially without absorption and is absorbed by the copper phthalocyanine-doped core, thereby causing the haptic to fuse with the optic.

39. The method of claim 38 wherein the optic comprises transparent plastic.

40. The method of claim 37 wherein the plastic comprises polymethylmethacrylate.

41. The method of claim 39 wherein the plastic comprises polycarbonate.

42. The method of claim 39 wherein the plastic comprises copolymers of esters of acrylic acid and methacrylic acid.

43. The method of claim 38 wherein a shape of the optic is a close curve.

44. A method for attaching at least one colored haptic to optic of an intraocular lens, comprising the steps of:
   a. forming the haptic from polymethylmethacrylate with a copper phthalocyanine-doped core;
   b. drilling a peripheral edge of the optic with at least one hole;
   c. inserting an end of the haptic into the hole;
   d. aiming at a portion of the haptic within the hole a Krypton laser having a power level of less than 5 watts and emitting radiation within the visible spectrum that is matched to the radiation absorption spectrum of the colored haptic; and
   e. firing the laser so that the radiation passes through the optic essentially without absorption and is absorbed by the copper phthalocyanine-doped core, thereby causing the haptic to fuse with the optic.

45. The method of claim 44 wherein the optic comprises transparent plastic.

46. The method of claim 45 wherein the plastic comprises polymethylmethacrylate.

47. The method of claim 45 wherein the plastic comprises polycarbonate.

48. The method of claim 45 wherein the plastic comprises copolymers of esters of acrylic acid and methacrylic acid.

49. The method of claim 44 wherein a shape of the optic is a closed curve.

50. A method for attaching at least one colored haptic to an optic of an intraocular lens, comprising the steps of:
   a. forming the haptic from polymethylmethacrylate with a copper phthalocyanine-doped core;
   b. drilling a peripheral edge of the optic with at least one hole;
   c. inserting an end of the haptic into the hole;
   d. aiming at a portion of the haptic within the hole a tunable dye laser having a power level of less than 5 watts and emitting radiation with a visible wavelength that is matched to the radiation absorption spectrum of the colored haptic; and
   e. firing the laser so that the radiation passes through the optic essentially without absorption and is absorbed by the copper phthalocyanine-doped core, thereby causing the haptic to fuse with the optic.

51. The method of claim 50 wherein the optic comprises transparent plastic.

52. The method of claim 51 wherein the plastic comprises polymethylmethacrylate.

53. The method of claim 51 wherein the plastic comprises polycarbonate.

54. The method of claim 51 wherein the plastic comprises copolymers of esters of acrylic acid and methacrylic acid.

55. The method of claim 50 wherein a shape of the optic is a closed curve.

* * * * *